(12) United States Patent
Owens et al.

(10) Patent No.: US 7,846,715 B2
(45) Date of Patent: Dec. 7, 2010

(54) SAMPLE CHAMBER VOLUME REDUCER

(76) Inventors: Aaron M. Owens, 200 Nathan La., Apt. 268, Plymouth, MN (US) 55441; Chrysanthi Williams, 360 Carlson Pkwy., Apt. 314, Minnetonka, MN (US) 55305; Troy D. Nickel, 5801 Pillsburg Ave., Minneapolis, MN (US) 55419

( * ) Notice: Subject to any disclaimer, the term of this patent is extended or adjusted under 35 U.S.C. 154(b) by 236 days.

(21) Appl. No.: 12/120,139

(22) Filed: May 13, 2008

(65) Prior Publication Data

US 2009/0286306 A1 Nov. 19, 2009

(51) Int. Cl.
*C12M 1/00* (2006.01)
(52) U.S. Cl. ............... 435/283.1; 435/284.1; 435/293.1; 73/863.71; 623/911
(58) Field of Classification Search ............... 73/863.71; 435/283.1, 284.1, 293.1, 325, 395; 210/283, 210/416.1; 623/911, 917, 925
See application file for complete search history.

(56) References Cited

U.S. PATENT DOCUMENTS

| 5,308,758 | A  | * | 5/1994  | Dahl ........................... 435/30 |
| 2002/0106718 | A1 | * | 8/2002  | Gombrich et al. .......... 435/40.5 |
| 2004/0069076 | A1 | * | 4/2004  | Gamble .................... 73/863.85 |
| 2005/0263406 | A1 |   | 12/2005 | Ameen et al. |
| 2008/0097371 | A1 | * | 4/2008  | Shemesh ..................... 604/414 |

OTHER PUBLICATIONS

International Search Report and Written Opinion dated May 7, 2010 for PCT/US09/037523.
International Search Report on Patentability for PCT/US2009/037523, dated Aug. 26, 2010, 9 pages.

* cited by examiner

*Primary Examiner*—William H Beisner
*Assistant Examiner*—Michael Hobbs (57) ABSTRACT

An apparatus includes a chamber insert capable of being received by a sample chamber of a conditioning system. The received chamber insert reduces the volume of the sample chamber and defines a cavity that substantially surrounds a sample holder located in the sample chamber.

11 Claims, 7 Drawing Sheets

SAMPLE CHAMBER VOLUME REDUCER

BACKGROUND

This description relates to a device that reduces the volume of a sample chamber and the amount of content needed to fill the volume.

With the expansion of tissue engineering, biomaterial research, and other areas of biotechnology, bioreactors have been developed for conditioning biologic specimens. By incorporating a sealable chamber into a bioreactor, fluids and other content can be introduced into the conditioning of specimens. As such, the conditioning may include placing biologic samples into a stationary or flowing fluid to simulate blood flow, synovial fluid flow or other fluid associated environment.

SUMMARY

In general, in one aspect, an apparatus includes a chamber insert capable of being received by a sample chamber of a conditioning system. The received chamber insert reduces the volume of the sample chamber and defines a cavity that substantially surrounds a sample holder located in the sample chamber.

Implementations may include one or more of the following features. The chamber insert may include two or more segments, which when combined, define the cavity. The chamber insert may include a feature for directing fluid flow such as a coating, a ridged surface, etc. For a feature such as a ridged surface, the ridges may be substantially parallel. The parallel ridges may also direct fluid to flow over a specimen in a spiral manner. The sample chamber may include a chamber window. The chamber insert may include one or more openings that substantially aligns with the chamber window. The chamber insert may includes one or more types of materials such as synthetic material, plastic material, materials to reduce adhesion of cellular material, materials to promote adhesion of cellular material, materials that are degradable, etc. The chamber insert may be produced to be disposable after one or more uses.

In general, in one aspect, a conditioning system includes a sample chamber capable of receiving a specimen, and, one or more ports capable of providing a fluid to the sample chamber. The conditioning system also includes a chamber insert capable of being received by the sample chamber. The received chamber insert reduces the volume of the sample chamber and defines a cavity that substantially surrounds a sample holder located in the sample chamber.

Implementations may include one or more of the following features. The chamber insert may include two or more segments, which when combined, define the cavity. The port may provide a fluid to an exterior surface or an interior surface of the specimen. The chamber insert may include a feature for directing fluid flow over the specimen. The feature may include a ridged surface that includes substantially parallel ridges. The sample chamber may include a chamber window and the chamber insert may include an opening that substantially aligns with the chamber window. The chamber insert includes one or more types of material such as a plastic material.

In general, in one aspect, an apparatus includes a chamber insert capable of being received by a sample chamber of a conditioning system. The chamber insert includes a section of the sample chamber. The received chamber insert reduces the volume of the sample chamber and defines a cavity that substantially surrounds a sample holder located in the sample chamber.

Implementations may include one or more of the following features. The chamber insert may include two (or more) segments, in which a first segment includes a first wall section of the sample chamber and a second segment includes a second wall section of the sample chamber. The first wall section and the second wall section may form the section of the sample chamber. The chamber insert may include one or more types of material such as a transparent material.

These and other aspects and features and various combinations of them may be expressed as methods, apparatus, systems, means for performing functions, and in other ways.

Other features and advantages will be apparent from the description a the claims.

DETAILED DESCRIPTION

Figure 1:
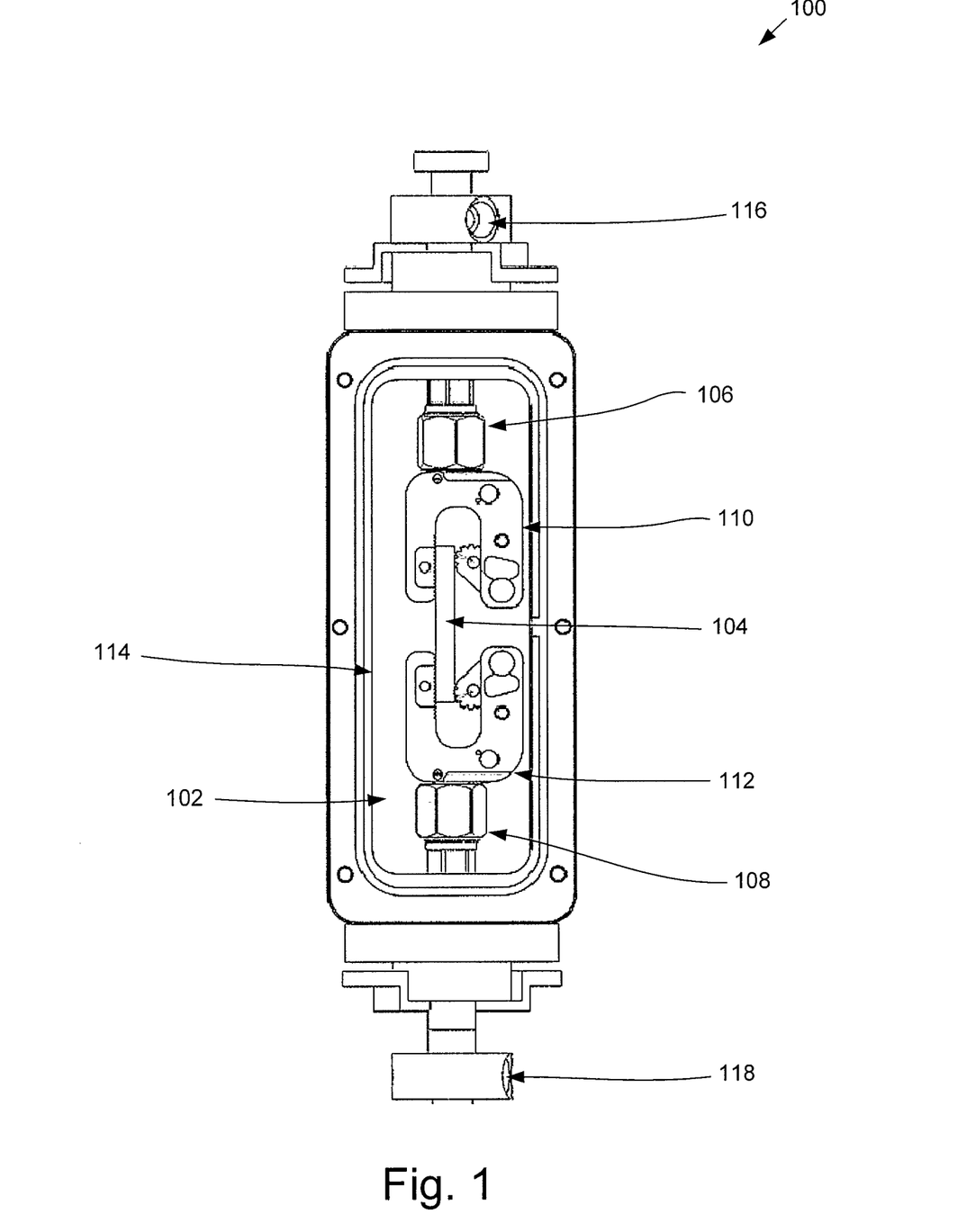
FIGS. 1 and 2 show sample chambers for conditioning specimens.

Referring to FIG. 1, a sample chamber 100 allows various types of tissues and other types of biomaterials to be conditioned. For example, specimens of blood vessels, cardiac muscle, bone, cartilage, spinal discs, tendons, skin, ligaments, trachea, heart valves or other types of material (e.g., tissue substitutes such as synthetic biomaterials) may be inserted and conditioned in the sample chamber 100. In general, for conditioning, a user-defined conditioning profile specifies a desired mechanical stimulation of a sample. The conditioning profile may specify a desired stress or strain state applied to the sample and may vary in time. If a cyclic conditioning protocol is desired, the conditioning profile may describe a desired stress or strain state over a user-specified cycle and the profile repeated for a user-specified number of cycles.

One or more contents such as fluids or other media may be introduced into the sample chamber 100 for simulating environmental conditions typically experienced by a sample. For example, a specimen inserted into the sample chamber 100 may be immersed in a fluid to simulate the blood surrounding the sample under conditioning. Fluid flow may also be simulated within the sample chamber 100. For example, a flow loop may be connected to the sample chamber 100 to provide flow over a specimen. Flow may also be directed through a specimen, for example, fluid may be directed through a tubular sample (e.g., blood vessel) that is under conditioning within the sample chamber 100. As such, for this arrangement the sample chamber 100 is sealable to allow for fill content and directed flow.

In this arrangement, to allow for the introduction of fluids (or other content), the sample chamber 100 is sealed to define a chamber volume 102 within which a specimen 104 is positioned. The sample chamber 100 also includes two push rods 106, 108 that allow for the specimen 104 to be held along an axis (here a vertically oriented axis). Along with assisting with mechanical stimulation (e.g., applying a load, displacement, pressure), the orientation and position of the push rods 106, 108 may be manually changed for adjusting the specimen 104. For this particular measurement, the ends of the specimen 104 are held by a pair of sample grips 110, 112 to allow for a load to be placed on the specimen (along with assisting other types of mechanical conditioning). While the "c-shaped" grips 110, 112 are relatively large compared to the chamber volume 102, other types of grips and gripping techniques may be used within the sample chamber 100.

The sample chamber 100 also includes a chamber window 114 that allows the chamber volume 102 (and the specimen 104 under conditioning) to be viewed, of example, during conditioning. Various types of transparent material (e.g., plastics, glass, etc.) may be used to produce the window 114 while still providing the appropriate structural integrity needed for conditioning with the sample chamber 100. Along with allowing the chamber volume 102 (and the contents of the volume) to be viewed, the chamber window 114 may also be used for non-intrusive conditioning of the specimen. For example, measurements that implement optical equipment (e.g., a laser, video extensometer, etc.) may utilize the chamber window 114 for accessing the chamber volume 102.

One or more ports may also be included in the sample chamber 100 for introducing fluids (or other types of contents) into the chamber volume 102. For example, one port 116 may be located at the top of the sample chamber 100 and another port 118 may be located at the bottom of the sample chamber. In this arrangement, the ports 116, 118 may be connected to a flow loop for introducing flow through a specimen (e.g., a vascular graft) as described with respect to FIG. 2. Other ports may also be included in the sample chamber 100 for filling the chamber volume 102 with one or more fluids (or other types of contents). For example, one or more ports may be incorporated into one or more walls of the sample chamber 100 or the chamber window 114 to provide fill fluid into the chamber volume 102.

Figure 2:
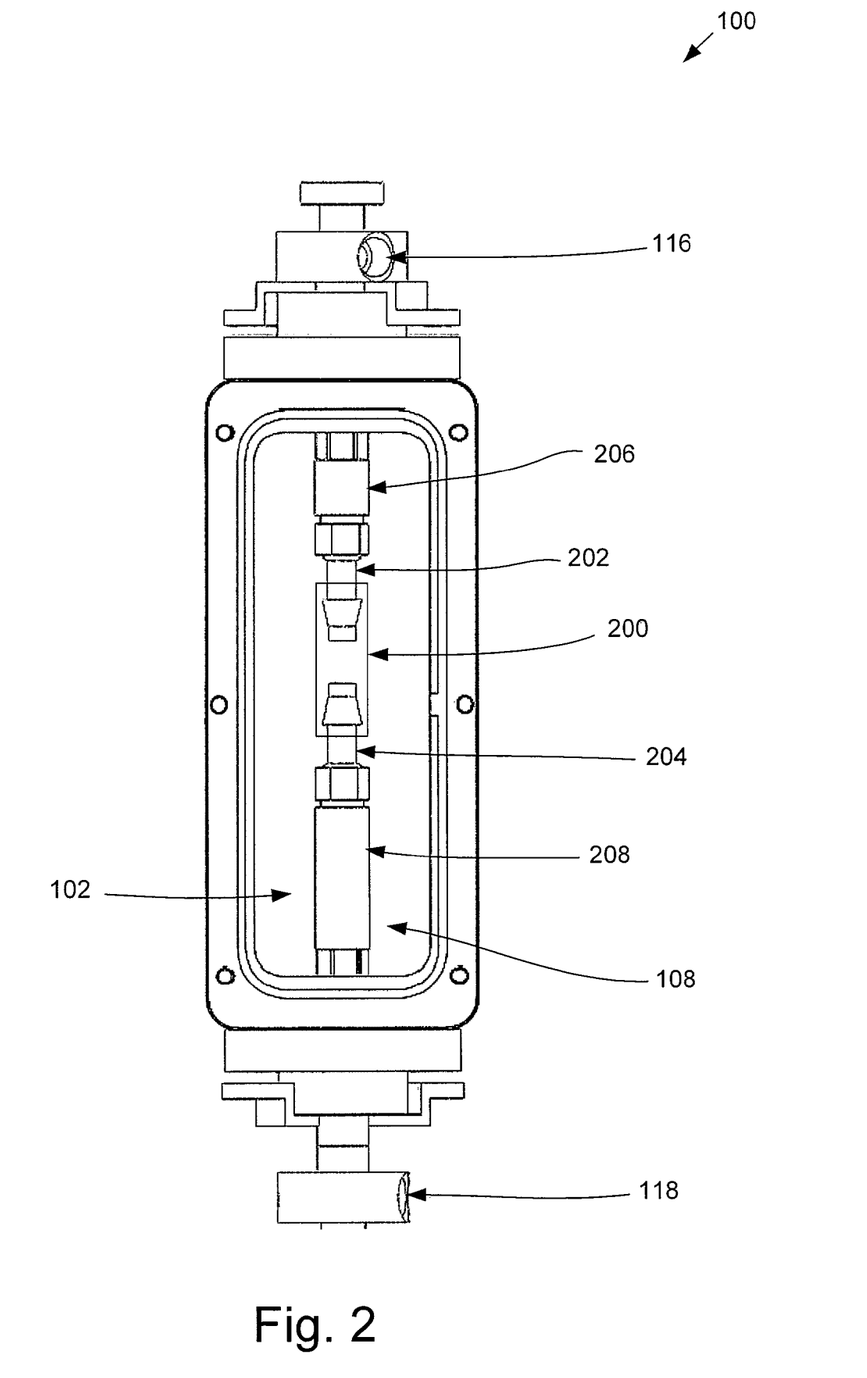

Referring to FIG. 2, the sample chamber 100 is configured for introducing a fluid flow through a specimen 200 under conditioning. Typically, to provide such a flow, the specimen 200 has a tubular geometry such as found with a trachea, a blood vessel, a bladder, etc. or similar geometry such as found with heart valve tissue or various types of tissue substitutes. In this particular arrangement, two fittings 202, 204 (e.g., nozzles, barb fittings, etc.) are respectively connected to two push rods 206, 208 to provide an entrance and exit pathway for the fluid. For example, fluid from a flow loop may be provided to the port 116 and passed into the specimen 200 via the push rod 206 and the fitting 202. To return the fluid to the flow loop (or to be passed to another destination), upon exiting the specimen 200, the fluid passes through the fitting 204 and the push rod 208 (which is in fluid communication with the port 118).

Similar to the configuration presented in FIG. 1, a noticeable amount of the chamber volume 102 is unused when configured for conditioning as shown in FIG. 2. Returning briefly to FIG. 1, while the push rods 106, 108, the sample grips 110, 112 and the specimen 104 populate the real estate of the chamber volume 102, a portion of the volume remains empty. More noticeably, in FIG. 2, a considerably smaller portion of the chamber volume 102 is populated with the push rods 206, 208, the fittings 202, 204 and the specimen 200 while the remaining portion is empty. Such unused space of the chamber volume 102 may be of assistance for a technician when inserting and removing contents. For example, the sample chamber 100 may be designed such that the chamber volume 102 allows for easy access and rapid mounting of components (e.g., push rods, grips, etc.) and the specimen under conditioning. However, once assembled for conditioning, the empty portion of the chamber volume 102 may introduce a considerable and undesired cost. For example, conditioning may call for considerably expensive fluid or media to cover the specimen under conditioning. Expensive fill contents such as a nutrient medium may be commercially available or custom produced may be needed for conditioning a specimen. Such contents may include material such as saline solutions, nutrients (e.g., vitamins, amino acids, etc.), pH buffering reagents, growth factors, anti-fungal and anti-bacterial agents and other types of components. In one example, the cost of a nutrient media may exceed $1.00 per milliliter. Accordingly, conditioning four samples in a one liter flow loop volume may cost approximately $1000.00. Thus, by reducing the unused portion of the chamber volume 102 during conditioning, a considerable cost saving may be realized.

Figure 3:
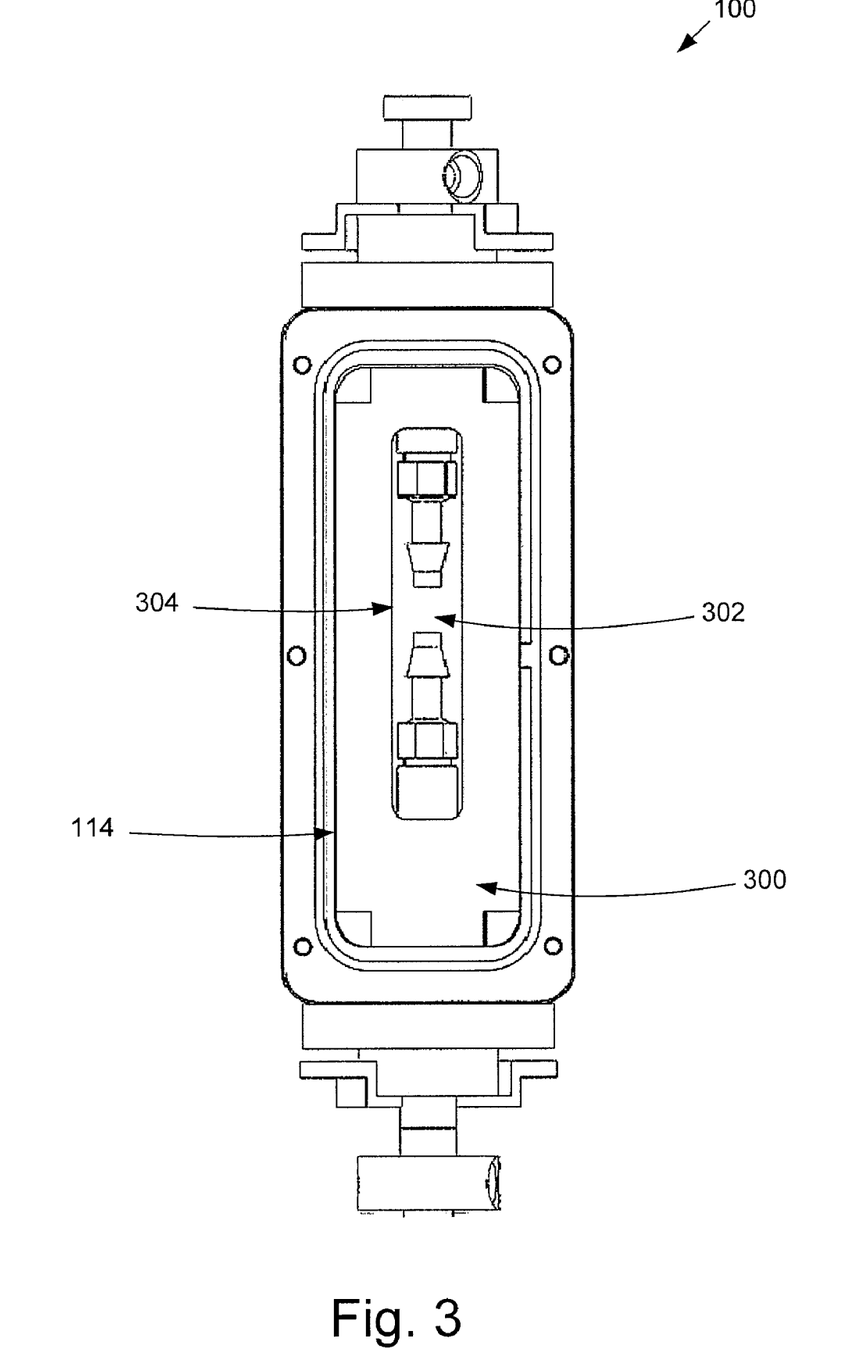
FIG. 3 shows a chamber insert positioned in a sample chamber.

Referring to FIG. 3, a chamber insert 300 is positioned into the sample chamber 100 to reduce the chamber volume without interfering with the specimen under conditioning and the devices for holding the specimen within the sample chamber. By reducing the volume, the amount of fluid or media needed to cover the specimen is significantly reduced, thereby reducing overall experimental cost. In this example, the chamber insert 300 occupies a considerable portion of the chamber volume. However, the portion of the chamber volume used for conditioning the specimen is not significantly encroached upon by the chamber insert 300. Rather, the chamber insert 300 defines a cavity 302 that surrounds the specimen and the devices for holding the specimen. In this particular example, the sample chamber 100 is configured for conditioning as shown in FIG. 2, in which the specimen is being held by a pair of push rods and fittings. By defining the cavity 302, the amount of fill fluid or media needed to cover a specimen under conditioning is reduced. Further, the cavity 302 allows fluid to flow through and/or over the specimen under conditioning. For example, the cavity 302 may be defined by the chamber insert 300 such that fluid (e.g., nutrient media) is maintained over the specimen and specimen holding devices (e.g., push rods, grips, porous or non-porous compression platens, nozzles, fittings such as barb fittings, three or four point bend fixtures, etc.). Further, the chamber insert 300 does not substantially come into contact (if at all) with the specimen or the holding devices. In some arrangements, the chamber insert is sufficiently fixed inside the chamber and remains substantially stationary with respect to the sample chamber during mechanical conditioning and/or fluid flow. In other arrangements, the chamber insert may be shaped or produced of materials to allow movement within the sample chamber during mechanical conditioning and/or fluid flow without significantly affecting the specimen e.g., while allowing fluid mixing to be enhanced.

Along with defining the cavity for conditioning, the chamber insert 300 may also include other features that assist specimen conditioning. For example, an opening 304 may be included in the chamber insert 300 to allow for viewing and for granting non-intrusive measurement devices (e.g. a laser micrometer, video extensometer, etc.) access to the specimen under conditioning. In this particular example, the opening 304 is aligned with the chamber window 114 of the sample chamber 100 to allow viewing of the specimen and the holding devices (e.g., push rods, fittings, etc.), however, in other arrangements different orientations, positions and opening sizes may be implemented. Additionally, more than one opening may be incorporated into the chamber insert 300 to provide viewing and access. For example, a series of relatively small openings may be included in the chamber insert 300 that are capable of receiving various types of transducers (e.g., pressure transducers) and flow measuring devices (e.g., hot wire, hot films, etc.). In some arrangements, viewing the specimen or specimen holding devices may not be needed and the opening 304 may be removed from the chamber insert 300. In some situations, a plug or other type of cover may be inserted into the opening 304, or, a chamber insert may be used that is absent such an opening. By eliminating the opening 304, the volume of the sample chamber is further reduced, thereby further reducing the fluid (e.g., nutrient media) needed to fill the chamber. The chamber insert 300 may also be manufactured such that the material is transparent to allow for viewing the interior of the sample chamber.

Figure 4A:
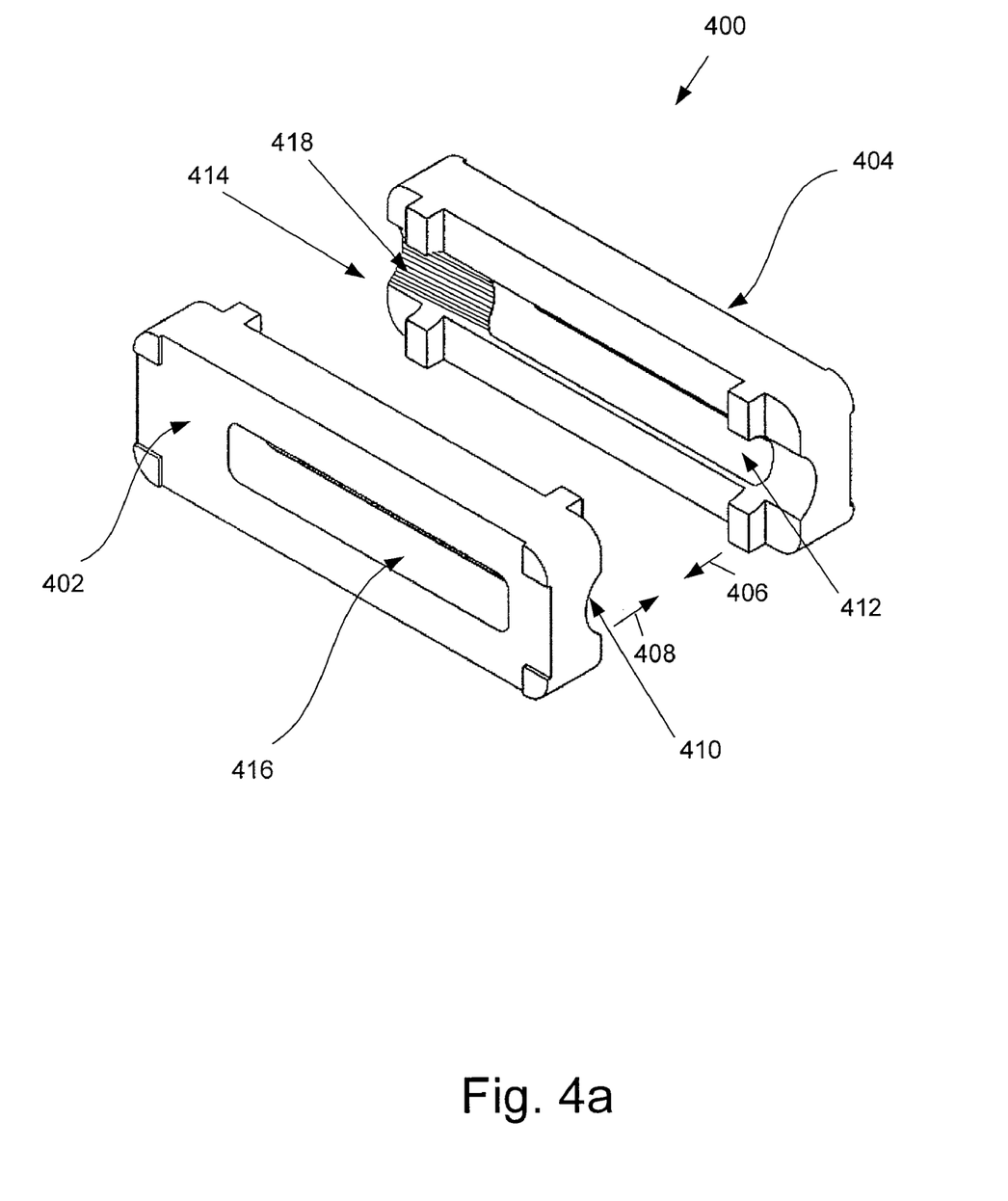
FIGS. 4a and 4b show exemplary chamber inserts.
Figure 4B:
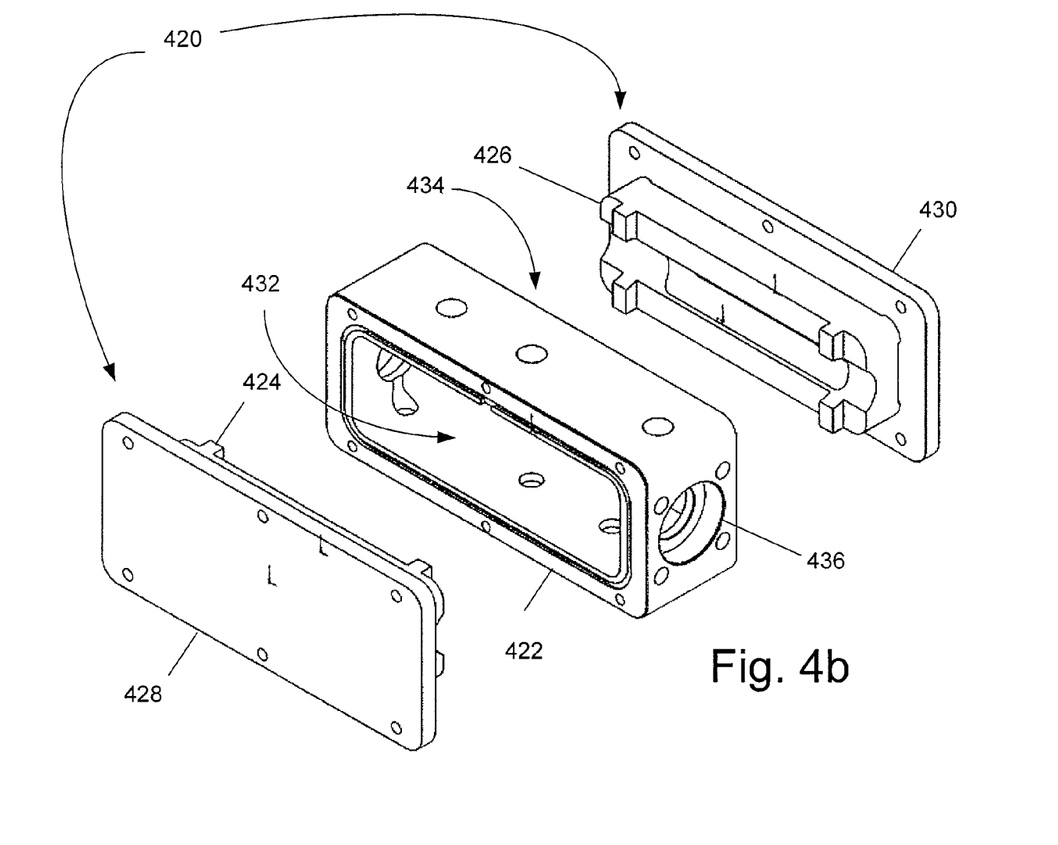

One or more implementations and techniques may be used for positioning a chamber insert (or multiple chamber inserts) within a sample chamber. For example, as represented in FIG. 4a, a chamber insert may be positioned within a sample chamber and enclosed by the walls of the sample chamber. A chamber insert may be produced that includes a portion that conforms to a sample chamber. For example, as represented in FIG. 4b, a sample chamber insert is produced (e.g., manufactured) that includes a portion of a sample chamber wall. As such, a portion of the chamber insert may be positioned within a sample chamber to reduce volume of the chamber while another portion of the insert forms a wall of the chamber.

Referring to FIG. 4a, one exemplary chamber insert 400 is illustrated as being a combination two segments 402, 404 that may be combined before or during insertion into a sample chamber. By segmenting the chamber insert 400, the segments 402, 404 may be positioned into the sample chamber with relative ease by a technician. During insertion, the segments 402, 404 may be positioned on opposing sides of the specimen holding device and moved (as indicated with arrows 406, 408) to form the chamber insert 400 and surround the holding devices and a specimen. While the chamber insert 400 is formed from two segments in this example, in some arrangements more than two segments may be produced and combined to form the chamber insert. A chamber insert may also be produced as a single segment that may have mechanical and material properties to allow insertion into a sample chamber. For example, a single piece chamber insert may be produced from one or more flexible materials (e.g., a flexible plastic) that may be physically manipulated for placing the insert into a chamber.

To receive the specimen and holding devices, one or more features may be incorporated into either or both of the segments 402, 404. For example, each of the segments 402, 404 may be shaped such that when combined, a cavity is formed to receive the specimen and the specimen hold devices. In this particular example, each segment respectively includes a channel 410, 412 that form a cylindrical cavity 414 upon combining the segments. Along with receiving the specimen and specimen holding devices, in this arrangement, the cylindrical cavity 414 provides a fluid flow path. In particular, the channels 410, 412 are open at each end of the two segments 402, 404 resulting in the cylindrical cavity 414 being open at each end and capable of supporting a fluid flow. As such, specimens positioned in the cylindrical cavity 414 may be immersed in fluid or content (e.g., nutrient media) for measurements. Additionally, by connecting the sample chamber into a flow loop, fluid may be circulated over and/or through the specimen.

Along with defining one or more cavities, other applications may be provided by features incorporated into the segments 402, 404. For example, features may be incorporated into one or more surfaces of the segments 402, 404 for directing the flow of fluid through the chamber insert 400. One or more coatings may be applied to surfaces that form the channels 410, 412. Incorporated features may also include structures incorporated into the channel surfaces, for example, ridges or fins may be formed (e.g., grooved) into the surfaces for directing fluid flow. As shown in the figure, in one exemplary arrangement, ridges 418 may be positioned into a parallel orientation to provide a relatively straight fluid flow (e.g., laminar flow) through a portion of the cylindrical cavity 414 and over the specimen. The parallel ridges may also be oriented and shaped to provide other types of flow. For example, a corkscrew pattern may be incorporated into the parallel ridges so that a spiral flow pattern is provided over the specimen. Structures may also be incorporated for producing a turbulent flow and providing surfaces (e.g., wings, spoilers, large eddy break up devices (LEBUs), etc.) for controlling the flow. A combination of coatings and structures may also be incorporated into the surfaces of channels, for example, a coating that includes series of parallel groves (e.g., riblets) may be applied for flow shaping and control.

Referring to FIG. 4b, rather than being positioned within a sample chamber as a separate structure, a chamber insert may be produced that includes one or more portions of a sample chamber. In this particular example, a chamber insert 420 includes two segments 424, 426 (similar to the chamber insert segments shown in FIG. 4a) that respectively include wall sections 428, 430 of a sample chamber 422. By producing such a chamber insert that includes conforming wall sections, the chamber insert segments 424, 426 form the sample chamber 422 along with forming the chamber insert 420 to reduce chamber volume. In this example, the sample chamber 422 is formed by inserting the chamber insert segments 424, 426 into respective openings 432, 434. Also, by inserting the segments 424, 426, a cavity is formed in the sample chamber 422 that surrounds a specimen and specimen holding devices. For viewing the specimen and specimen holding devices, transparent or semi-transparent material may be incorporated into one (or both) of the chamber insert segments 424, 426 and one (or both) of the corresponding sample chamber wall sections 428, 430 (or both). In some arrangements, a portion of a chamber insert segment (e.g., segment 424) may be removed (e.g., cut out) to produce an opening that may be aligned with a transparent portion (e.g., a window) of a sample chamber wall section (e.g., section 428) for viewing a specimen. Other features may also be included in the sample chamber 422, for example, in this particular arrangement a grip point 436 is included in the sample chamber to allow access to the interior of the chamber.

Surface features and treatments may also be incorporated that are specific to the fluid being introduced to the specimen (e.g., covering, passing over, etc.). For example, the fluid may include a nutrient media that contains live cellular material. As such, the surface of channels (e.g., channels 410, 412) may need to be formed of a material that is substantially inert to such cellular material. The surfaces of the channels may have a relatively smooth finish so that cellular material (e.g., individual cells) is not impeded by or lodged in a surface defect (e.g., surface pit, pore, etc.) and possibly contaminate the remaining fluid (and possibly the specimen). In some arrangements, a coating (which is capable of preventing cell adhesion to surfaces) may be applied to one or more chamber insert surfaces so that cells are suspended in the fluid and do not significantly adhere to the surfaces. Exemplary materials that prevent cell adhesion include heparin and Sigmacote.

One or more coatings may also be applied for promoting the adhesion of cells on insert surfaces (e.g., for producing molecules beneficial to the specimen). Such materials may be produced by processing biologic structures so that cells substantially attach to these materials. Adhesion promoting materials include growth factors (e.g., vascular endothelial growth factor), proteins (laminin, fibronectin), peptide sequences (e.g., RGD) and other similar molecules. Chamber insert surfaces may be treated with one or more chemicals (e.g., heparin), coatings, etc. so that blood can be used in a sample chamber without significant coagulation. Further, a chamber insert may have a defined porosity and pore size distribution that promote fluid flow mixing and particular flow profiles. Further, a chamber insert may contain defined pores that are used to encapsulate nutrients for slow release over a period of time (e.g., nutrients encapsulated in degradable materials so that their release is dependent on the material's degradation rate). Relatively inexpensive material may also be used for producing chamber inserts, for example, polystyrenes or other similar material may be used to produce inserts. As such, the chamber inserts may be considered relatively inexpensive and disposable (e.g., may be discarded after one or a few uses).

In some arrangements the insert or portions of the insert may be degradable such that over a period of time (and in some arrangements a controllable period of time), the chamber insert degrades away. Such an arrangement may support measurements during which cell numbers and/or metabolic activity may have significantly increased and higher nutrient medium volumes are needed. In some arrangements, such degradable chamber inserts may include materials with characteristics such as biocompatible, autoclavable, a relatively small amount of surface defects per unit area, etc. Degradable materials include, e.g., polyglycolic acid, polylactic acid, polycaprolactone, etc.

Features may also be incorporated into the insert segments (e.g., segments 402, 404) for providing access to the specimen and the specimen holding devices. For example, portions of segments may be removed (e.g., cutout) or segments may be created to produce one more openings. Similar to the opening 304 (shown in FIG. 3), segments (e.g., segment 402) may include an opening to allow viewing of and non-intrusive access to the location of the specimen. Features may also include other types of openings or partial openings for accessing the vicinity of the specimen. For example, one opening or an array of openings may be incorporated into one or more of the segments 402, 404 for providing access to measurement devices (e.g., pressure sensors) and flow monitoring devices (e.g., hot films, hot wires, etc.).

Various types of material may used to produce a chamber insert (e.g., chamber insert 400) and corresponding segments. One or more synthetic materials such as glass, plastics and thermoplastics may be used to produce the segments (e.g., segments 402, 404). For example, polyethylene, polypropylene (e.g., TecaPro™ from Boedeker Plastics, Inc of Shiner, Tex.) or other similar plastic may be used. Particular material characteristics may be implemented to produce inserts, for example, non-porous, biocompatible, non-cytotoxic, chemically inert (non-corrosive), sterilizable (preferably by steam sterilization or autoclaving) material may be implemented.

Figure 5:
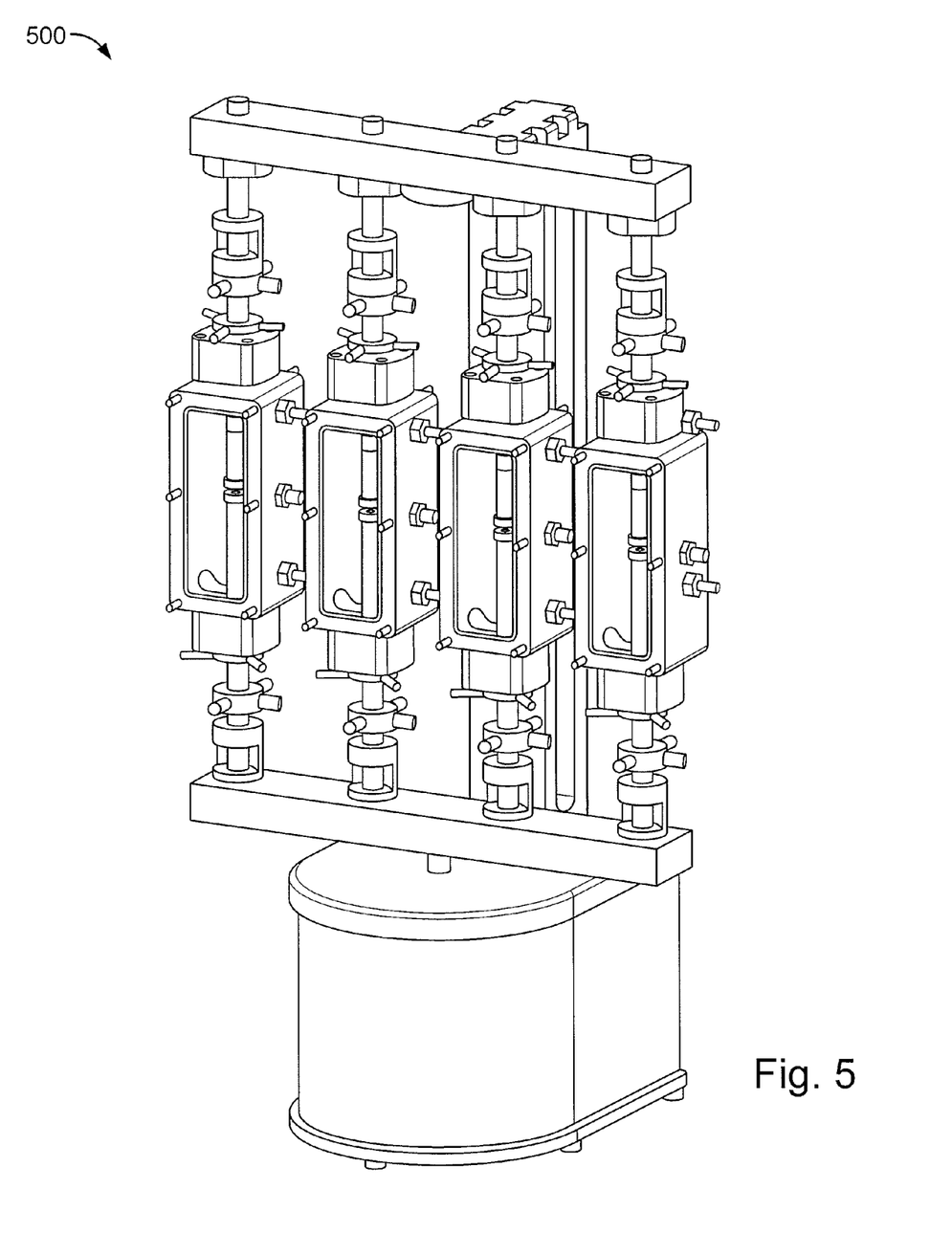
FIGS. 5 and 6 show exemplary conditioning systems that contain multiple sample chambers.
Figure 6:
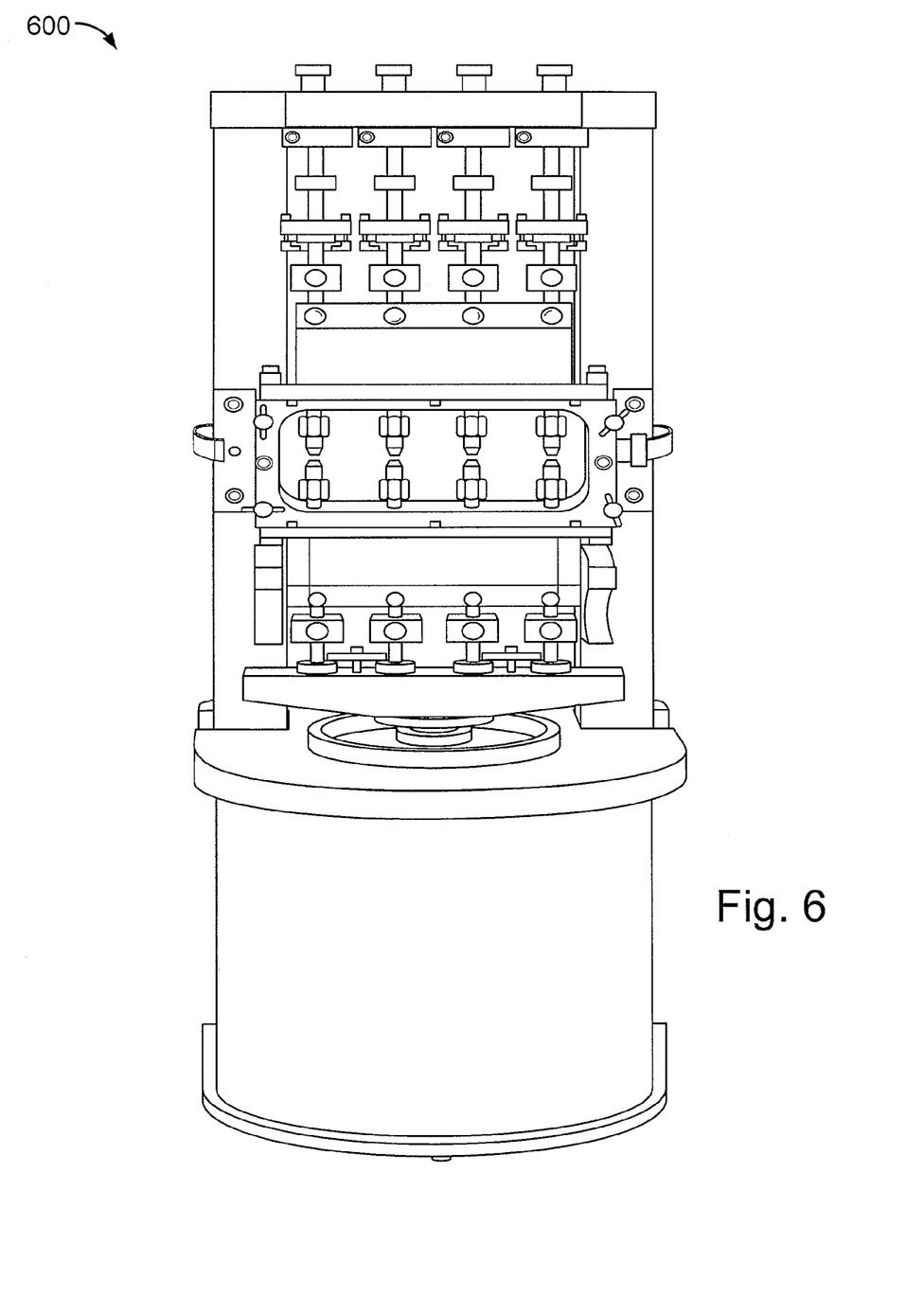

Referring to FIGS. 5 and 6, two implementations of conditioning systems are displayed that include multiple sample chambers similar to the sample chambers shown in FIGS. 1, 2 and 3. In particular, a conditioning system 500 is presented in FIG. 5 and includes four vertically oriented sample chambers. The conditioning system 500 includes sample chambers configured to condition disc-like samples (e.g., cartilage, bone, meniscus, etc.). FIG. 6 presents a conditioning system 600 that includes a multiple sample chamber along with flow loop equipment. Similar to the sample chamber shown in FIG. 3, a chamber insert may be positioned in one or more of the sample chambers of the conditioning systems 500, 600 to reduce the volume of the respective sample chambers and correspondingly reduce the amount of fill fluid and conditioning cost. Other implementations may also be used, such as conditioning systems described in U.S. patent application Ser. No. 11/780,729, now U.S. Pat. No. 7,587,949, filed Jul. 20, 2007, and U.S. application Ser. No. 12/119,830, now U.S. Pat. No. 7,694,593, entitled "Multi-Sample Conditioning System", filed May 13, 2008, both of which are herein incorporated by reference.

Other embodiments are within the scope of the following claims. The techniques described herein can be performed in a different order and still achieve desirable results.

What is claimed is:

1. A conditioning system comprising:
   a sample chamber capable of receiving a specimen;
   a first and a second specimen-holding fixture positioned within the sample chamber and configured to apply mechanical stimulation to a specimen held by the fixtures;
   at least one port capable of providing a fluid to the sample chamber; and
   a chamber insert capable of being received by the sample chamber, wherein the received chamber insert reduces the volume of the sample chamber and defines a cavity that substantially surrounds the first and second specimen-holding fixtures without contacting the specimen-holding fixtures or a specimen held by the fixtures.

2. The conditioning system of claim 1, in which in the chamber insert includes at least a first segment and a second segment that combine to define the cavity.

3. The conditioning system of claim 1, in which the port provides a fluid to an exterior surface of the specimen.

4. The conditioning system of claim 1, in which the port is coupled to the first specimen-holding fixture and provides a fluid to an interior surface of the specimen through the first specimen-holding fixture.

5. The conditioning system of claim 1, in which the chamber insert includes a feature for directing fluid flow over the specimen.

6. The conditioning system of claim 5, in which the feature includes a ridged surface that includes substantially parallel ridges.

7. The conditioning system of claim 1, in which the sample chamber includes a chamber window and the chamber insert includes an opening that substantially aligns with the chamber window.

8. The conditioning system of claim 1, in which the chamber insert includes a plastic material.

9. The apparatus of claim 1 in which
   the chamber insert includes at least a first segment and a second segment, wherein the first segment forms a first wall section of the sample chamber and the second segment forms a second wall section of the sample chamber when the chamber insert is installed in the sample chamber.

10. The apparatus of claim 1 in which
    the first and the second specimen-holding fixture each comprise a grip for holding a respective end of a specimen, and
    at least the first specimen-holding fixture is configured to apply the mechanical stimulation to the specimen by transmitting an axial load to the specimen.

11. The apparatus of claim 1 in which
    the first and the second specimen-holding fixture each comprise a fitting including a pathway for fluid, and
    the specimen-holding fixtures are configured to apply the mechanical stimulation to the specimen by directing a flow of fluid through the specimen.

* * * * *